US00PP08938P

United States Patent [19]

Drewlow

[11] Patent Number: Plant 8,938

[45] Date of Patent: Oct. 11, 1994

[54] IMPATIENS PLANT NAMED TEMPEST

[75] Inventor: Lyndon W. Drewlow, Ashtabula, Ohio

[73] Assignee: Mikkelsens, Inc., Ashtabula, Ohio

[21] Appl. No.: 165,589

[22] Filed: Dec. 13, 1993

[51] Int. Cl.[5] ..... A01H 5/00
[52] U.S. Cl. ..... Plt./87.6
[58] Field of Search ..... Plt. 87.6

*Primary Examiner*—James R. Feyrer
*Attorney, Agent, or Firm*—Foley & Lardner

[57] ABSTRACT

A new and distinct cultivar of Impatiens plant named Tempest, characterized by its relatively large diameter red and very light pink bicolor flowers, a standard petal which is larger than the other petals, dark green leaves with heavy greyed-orange variegation around the midrib, early flowering habit, highly self-branching and floriferous habits, flowering entirely above leaf canopy, tolerance to both high and cool temperatures, and its adaptability to be grown in 10 cm up to 15-25 cm containers.

1 Drawing Sheet

The present invention relates to a new and distinctive cultivar of Impatiens plant, botanically known as Impatiens, commercially known as New Guinea Impatiens, and known by the cultivar name Tempest.

The new cultivar was developed in a controlled breeding program conducted by the inventor Lyndon W. Drewlow in Ashtabula, Ohio. Tempest was created by crossing Mikkelsen Seedling No. 88-388-2 (seed parent) with Mikkelsen Seedling No. 90-343-1 (pollen parent). Both parents are proprietary cultivars used in the breeding program.

Asexual reproduction by terminal or stem cuttings carried out by or under the supervision of the inventor in Ashtabula, Ohio has shown that the unique features of Tempest are stabilized and are reproduced true to type in successive propagations.

The following combination of characteristics distinguish Tempest from both its parent varieties and other cultivated impatiens of this type known and used in the floriculture industry. Comparisons are made to the cultivars Twilight (U.S. Plant Pat. No. 5,869) and Sunburst (U.S. Plant Pat. No. 6,308).

1. Tempest has deep red (45A) and light pink (49D) bicolor flowers, with Twilight being a lighter red (40C) and light pink (49C) bicolor and Sunburst being an orange-red (34A) and light pink (40C) bicolor.

2. Tempest has the largest diameter flower at 6.0 cm to 6.5 cm, compared to the flower diameter of 5.0 to 5.25 cm for Twilight and 4.5 to 5.0 cm for Sunburst.

3. The leaves of Tempest are 13 cm to 14 cm in length by 3.5 cm to 4.0 cm in width, and are larger than the leaves Sunburst which are 11 cm to 12 cm long and 3.0 cm to 3.5 cm wide, and the leaves of Twilight which are 7.5 cm to 7.75 cm long and 3.0 cm to 3.25 cm wide.

4. The dark green leaves of Tempest have a greyed-orange (164A) variegation which covers two-thirds of the leaf around the midrib and at the basal end extending to the leaf margin. Twilight has greyed-yellow (160A) variegation around the midrib on the lower two-thirds of the leaf but the variegation does not extend to the margin. Sunburst only has a trace of greyed-yellow (160A) variegation around the midrib under high light conditions.

5. Tempest has glabrous leaf and stem surfaces as does Sunburst, while Twilight has tiny short hairs on leaf surface and on the stems.

6. Tempest has a plant height of 22 to 24 cm, taller than Sunburst which has a height of 18 to 20 cm but shorter than Twilight which has a plant height of 30 to 32 cm.

7. Tempest has a relatively vertical self-branching habit which produces a dense mounded plant. Both Sunburst and Twilight have more open and spreading growth habits.

8. Tempest is 7 to 10 days earlier to bloom than either Sunburst or Twilight.

9. In Tempest, the standard petal is the largest of the five petals. In Sunburst, the two keel petals and the standard petal are the largest and equal in size, and in Twilight all five petals are of equal size.

10. The flowers of Tempest are carried above the leaf canopy of the plant, while in both Sunburst and Twilight there are flowers inside the leaf canopy.

The accompanying colored photograph comprises a top perspective view and illustrates the overall appearance of Tempest, with the colors being as true as it is reasonably possible to obtain in a colored reproduction of this type. The photograph was taken in Ashtabula, Ohio on Sep. 24, 1993 under natural light in a shaded glass greenhouse under 40% saran on a sunny day.

The following is a detailed description of Tempest based on plants produced in greenhouses in Ashtabula, Ohio during the summer season of the year. Plants were grown in 15 cm pots and measurements were taken 18 weeks after rooted cuttings were planted. Height measurements were taken from the soil line of the container. The plants were grown at 65°-68° F. night temperatures under 3000-4000 foot candles of light, and with 250 ppm nitrogen, 75 ppm potassium, and 250 ppm phosphorus nutritional levels, with trace elements added. Habit of growth, foliage coloration, leaf variegation, size of leaves and flower size will be influenced by nutritional and environmental conditions, without, however, any variation in genotype.

Color references are made to The Royal Horticultural Society Colour Chart except where general terms of ordinary dictionary significance are used.

Parentage: A controlled cross between female parent Mikkelsen Seedling No. 88-388-2 and male parent Mikkelsen Seedling No. 90-343-1.

Propagation:

(A) *Type cutting.*—Stem tip 15 mm long will develop 4 to 5 cm long in 18 to 21 days.

(B) *Time to root.*—8–10 days at 23° C. summer; 10–12 days at 20° C. winter.

(C) *Rooting habit.*—Heavy, fibrous.

Plant description:

(A) *Form and habit growth.*—Mounded; highly self-branched; intermediate in height; flowers over the top of the leaf canopy; continuous flowering; vigorous growing flowering herb.

(B) *Foliage.*—Brownish green with bronze to cream variegation around midrib and basal part of leaf. Midrib, petiole and major veins are reddish purple. (1) Size: Average mature leaf is 13 cm to 14 cm long and 3.5 to 4.0 cm wide. (2) Shape: Lanceolate with acuminate apex and acute base. (3) Texture: Both upper and lower surfaces are glabrous. (4) Margin: Finely serrated with fine ciliate. (5) Color: Young foliage, top side 147A with reddish cast, under side 187A; mature foliage, top side 147A variegated with 164A, under side 187B. (6) Veination: Pinnate, red in color.

Flowering description:

(A) *Flowering habits.*—Flowers continuously from leaf whorl of usually 6 to 7 leaves in a progressively orderly manner. There is usually one flower per leaf axil but occasionally there are two flowers per leaf axil. When the last flower in the leaf whorl opens the first flower in the leaf whorl above starts to open. It takes 5 to 7 days for a mature bud to fully open and then the flower may last two weeks or longer depending on the environment.

(B) *Natural flowering season.*—Indeterminant and continuous. Quantity of flowering increases with increasing levels of light.

(C) *Flower buds.*—Ellipsoidal, flowers perfect; light green with reddish cast on upper one-third of 4.5 cm long spur on mature bud. The throat is behind the ovary and originates from the major sepal. Spur tip is darker green than rest of spur.

(D) *Flowers borne.*—On individual 4.0 cm light green pedicels from a whorl of 6 to 7 leaves, flowering progressively around the whorls as buds and leaves develop. Leaf axils have one flower each.

(E) *Quantity of flowers.*—Numerous because of highly self-branched nature of plant and long lasting flowers, with flowers open at two leaf whorls on a branch.

(F) *Diameter of flower.*—6.0 to 6.5 cm.

(G) *Petals.*—(1) Shape: Heart, standard petal is largest. (2) Color: Top side in summer when opening 45A and 49D bicolor, fading to 45A and 155D bicolor; under side 44C (3) Number of petals: Five (5). (4) Size of petals: Standard: 4.5 cm wide and 2.5 cm long; two equal lobes, moderate cut. Wings: 2.5 cm wide and 3.0 cm long; two unequal lobes, deep cut. Keel: 3.5 cm wide and 3.0 cm long; two unequal lobes, deep cut.

(H) *Reproductive organs.*—(1) Stamens: Five (5) in number (a) Anther: Hooded shape and color is reddish. (b) Pollen color: Cream. (2) Pistels (a) Stigma shape: Five (5) segmented column; color is purple red. (b) Style color: Purple red. (c) Ovaries: Five (5) in number, mature size 55 mm; color is dark green.

Disease resistance: No significant disease or insect problems noted to date.

OTHER IMPORTANT CHARACTERISTICS

1. Self-branching and early flowering habits of Tempest allow cultivar to be grown in 10 cm pots, but the cultivar is also vigorous enough to be grown in 15 to 25 cm containers as well.

2. Tempest has shown the ability to continue to bloom at both high temperatures and sunlight, as well as cool temperatures (40°–50° F.). Thus, the growing season of Tempest can be extended.

I claim:

1. A new and distinct cultivar of Impatiens plant named Tempest, as illustrated and described.

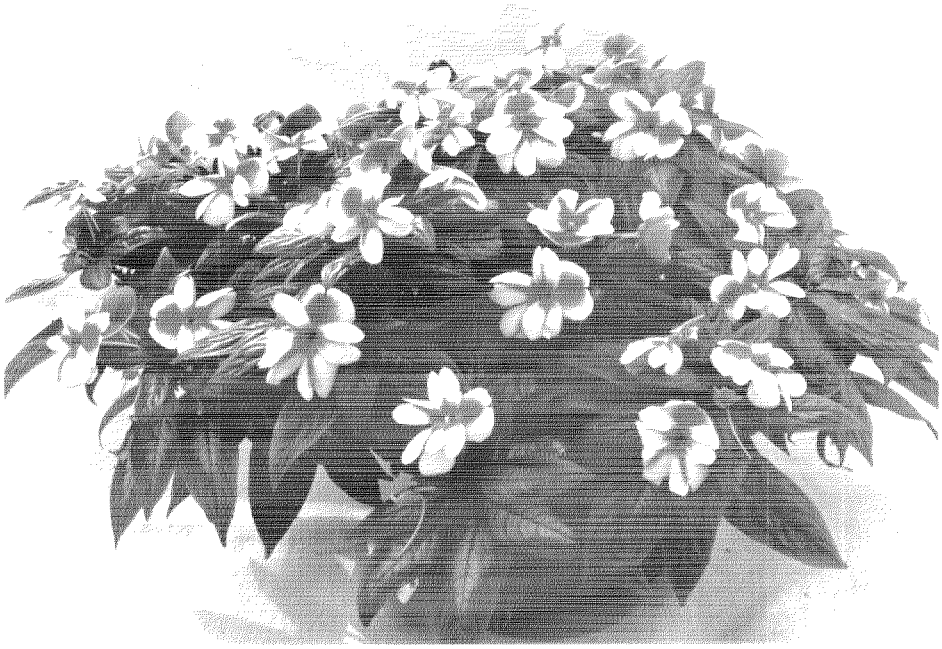

* * * * *